(12) United States Patent
Pamukcu et al.

(10) Patent No.: US 10,045,949 B2
(45) Date of Patent: Aug. 14, 2018

(54) MANAGING OSTEOPOROSIS WITH HMW PEG

(71) Applicants: MIDWAY PHARMACEUTICALS, INC., Spring House, PA (US); BOARD OF TRUSTEES OF MICHIGAN STATE UNIVERSITY, East Lansing, MI (US)

(72) Inventors: Rifat Pamukcu, Spring House, PA (US); Laura Rae McCabe, Haslett, MI (US)

(73) Assignees: MIDWAY PHARMACEUTICALS, INC, Spring House, PA (US); BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 14/768,741

(22) PCT Filed: Mar. 14, 2014

(86) PCT No.: PCT/US2014/028832
§ 371 (c)(1),
(2) Date: Aug. 18, 2015

(87) PCT Pub. No.: WO2014/144425
PCT Pub. Date: Sep. 18, 2014

(65) Prior Publication Data
US 2016/0000730 A1 Jan. 7, 2016

Related U.S. Application Data

(60) Provisional application No. 61/798,481, filed on Mar. 15, 2013.

(51) Int. Cl.
*A61K 31/047* (2006.01)
*A61K 9/00* (2006.01)

(52) U.S. Cl.
CPC .......... *A61K 31/047* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 8,153,112 | B2 | 4/2012 | Drapeau et al. |
| 2006/0198817 | A1 | 9/2006 | Alverdy |
| 2007/0258938 | A1 | 11/2007 | Roy et al. |
| 2008/0206188 | A1 | 8/2008 | Alverdy et al. |
| 2012/0078017 | A1 | 3/2012 | Alverdy et al. |

FOREIGN PATENT DOCUMENTS

| | | | |
|---|---|---|---|
| EP | 2468265 A2 * | 6/2012 | ........... A61K 9/0056 |
| JP | 10-338646 | 12/1998 | |
| JP | 2006-515837 | 6/2006 | |
| WO | 2004/105825 A1 | 12/2004 | |

OTHER PUBLICATIONS

Business Wire (published Dec. 3, 2009).*
National Comprehensive Cancer Network (available online at www.nccn.org, accessed Sep. 16, 2016).*
Business Wire (published May 17, 2006 (identified in Action as "Business Wire 2")).*
Sartor (J Clin Gastroenterol 41:S37-S43, 2007).*
Derwent Accession No. 2012-H06589 (Year: 2012).*
Humber, C., et al., "Bone Healing With an Insitu-Formed Bioresorbably Polyethylene Glycol Hydrogel Membrane in Rabbit Calvarial Defects," Oral and Maxillofacial Implants, vol. 109, No. 3, pp. 372-384 (Mar. 2010).
Murillo, A., et al., "Bone Resorptive Activity of Osteoclast-Like Cells Generated in Vitro by PEG-Induced Macrophage Fusion," Biol. Res., vol. 43, pp. 205-224 (2010).
von Tirpita, C., et al., "Management of Osteoporosis in Patients with Gastroinstestinal Diseases," European Journal of Gastroenterology & Hepatology, vol. 15, Issue 8, pp. 869-876 (Aug. 2003).
International Search Report of PCT/US2014/28832 dated Jul. 29, 2014.
Written Opinion of PCT/US2014/28832 dated Jul. 29, 2014.
International Preliminary Report on Patentability of PCT/US2014/28832 dated Sep. 15, 2015.

* cited by examiner

*Primary Examiner* — Craig D Ricci
(74) *Attorney, Agent, or Firm* — Polsinelli PC; John W. Campbell

(57) ABSTRACT

The present invention relates to the administration of compositions comprising polyethylene glycol, for improving the general gastrointestinal health of an animal increasing growth performance and treating osteopenia, osteoporosis and other bone disorders.

5 Claims, 16 Drawing Sheets

MicroComputed Tomography of Mouse Femurs control control + PEG OVX OVX + PEG

Serum Osteocalcin

HMW-PEG and recovery of bacteria from infected chickens

MANAGING OSTEOPOROSIS WITH HMW PEG

CROSS-REFERENCE TO RELATED APPLICATIONS

This application claims the benefit of U.S. Provisional Application No. 61/798,481 filed Mar. 15, 2013, the contents of which are incorporated herein by reference.

FIELD OF THE INVENTION

The present invention relates to materials and methods for preventing or treating disorders associated with changes in gastrointestinal health, including bone loss disorders such as osteopenia or osteoporosis by administration of high molecular weight polyethylene glycol (HMW PEG) compositions.

BACKGROUND

A substantial proportion of the elderly population will suffer fractures associated with low bone mass. [Ch. 4. The Frequency of Bone Disease. In: Bone Health and Osteoporosis: A Report of the Surgeon General. Rockville, Md.: U.S. Department of Health and Human Services, Office of the Surgeon General (2004)]. Ten million Americans 50 years of age and older already have osteoporosis and another 33 million have osteopenia, the total population with low bone mass is estimated to reach 61 million by 2020 [Khosla, et al., Journal of Bone and Mineral Research 26:2565 (2011)]. In 2005 almost 2 million osteoporosis-related fractures were reported. The number of such fractures is expected to exceed 3 million by 2025 [Khosla, et al., (2011)].

While osteopenia and osteoporosis are problems commonly associated with post menopausal women, they also occur in older men and in men suffering from low testosterone [Riggs, et al., Endocr. Rev. 23:279 (2002)]. Low bone mass is also a significant problem in those suffering from diseases of the gastrointestinal tract such as inflammatory bowel disease (IBD); including Crohn's disease, ulcerative colitis, pouchitis and microscopic colitis [reviewed in Ali, et al., Am. J. Med. 122:599 (2009)]. In addition, those that have undergone gastrectomy or small bowel resection, as well as patients undergoing corticosteroid therapy are at higher risk for osteopenia or osteoporosis [Coates, et al., J. Clin. Endocrinol. Metab. 89:1061 (2004); Ali, et al., (2009)].

The normal physiologic process of bone remodeling involves balancing rates of bone resorption and bone synthesis. Bone resorption is mediated by osteoclasts, whereas bone synthesis is largely carried out by osteoblasts. Typically, bone is maintained and damaged bone repaired by the coordinate actions of osteoclasts and osteoblasts. The first cell type facilitating resorption of damaged bone and the second synthesizing new bone. Osteopenia and osteoporosis occur when accelerated rates of bone resorption and declining rates of new bone synthesis alter the mineral content, density and structure of bone [Ch. 2. The Basics of Bone in Health and Disease. In: Bone Health and Osteoporosis: A Report of the Surgeon General (2004)].

A mouse model for post menopausal induced osteoporosis is available. This model involves removing the ovaries of young (approximately eight to twelve week old) mice to provoke estrogen deficiency. Within a few weeks of overiectomy, the mice exhibit significantly reduced bone mass and display all the morphological bone characteristics of osteoporosis, including highly increased incidence of low trauma fractures [Seidlova-Wuttke, et al., Comp. Med. 62:8 (2012)]. Another mouse model, directed at inducing IBD has also been found to produce osteopenia and osteoporosis. In this system, mice are treated with dextran sodium sulfate (DSS), usually by providing drinking water supplemented with a few percent DSS for a period of a few days or weeks [Hamdani, et al., Bone 43:945 (2008); Harris, et al., Am. J. Physiol. Gastrointest. Liver Physiol. 296:G1020 (2009)]. Mice that are exposed to DSS in drinking water will develop an inflammation of the colon, displaying symptoms such as diarrhea, rectal bleeding, and weight loss. Acute colitis can be induced by a single cycle of DSS exposure lasting only a few days; longer exposure or multiple cycles of exposure can result in chronic colitis.

These two mouse models provide the opportunity to examine the genesis and treatment of bone loss and bone disorders under two different physiologic conditions. The overiectomized mouse model allows investigation of osteopenia and osteoporosis in a system in which the chronic inflammation associated with IBD is absent, whereas the DSS system allows investigation of osteopenia and osteoporosis in which chronic inflammation of the gut, typical of IBD is the direct, though distal cause of bone loss. Both these animal models have proven to be useful tools for understanding the biological consequences of low bone density-related diseases and in the development of therapeutic and prophylactic treatments.

Hormone replacement therapy (HRT) was once the main treatment for osteopenia and osteoporosis in post-menopausal women, because it effectively rebalances bone resorption and new bone synthesis. Bisphosphonate compounds, such as risedronic acid (Actonel®), alendronic acid (Fosamax®), and pamidronic acid (Aredia®), have largely replaced HRT due to concerns that HRT may increase risk of cancer. Bisphosphonates conserve bone mineral density and reduce fracture risk by slowing the rate of bone resorption; however they do not stimulate new bone synthesis. Long term use of bisphosphonates may be harmful to overall bone health, since the normal bone remodeling process is inhibited and damaged bone is not efficiently repaired. For general discussion of the risks and benefits of bisphosphonates see National Osteoporosis Society "Drug Treatment" [National Osteoporosis Society. "Drug Treatment" Camerton, Bath BA2 OPJ United Kingdom, revised June 2012 (2012); Ch. 9. Prevention and Treatment for Those Who Have Bone Diseases. In: Bone Health and Osteoporosis: A Report of the Surgeon General (2004)].

Treatment of IBD frequently involves use of immunosuppressant glucocorticoids, which are known to adversely affect bone density [Long, et al., Dig. Dis. Sci. 55:2263 (2010)]. However, severe bone loss is apparent in untreated IBD sufferers and therefore is not a consequence of glucocorticoid treatment in these patients [Bjarnason, Rheumatology 38:801 (1999)]. Different kinds of IBD result in bone loss, indicating that the connection between the two pathologies is common to IBD in general and is not particular to Crohn's disease, ulcerative colitis, or any of the other specific conditions generally classified as IBD.

Interestingly, DSS treated mice appear to develop osteopenia by a reduction in bone formation, as opposed to an increase in bone resorption [Harris, et al., (2009)]. DSS induced IBD has been reported to not only reduce osteoblast activity but simultaneously increase the number of osteoclasts, most of which appear to be inactive [Harris, et al., (2009)]. These findings are supported by an alternative approach to assessing conditions associated with chronic systemic inflammation that does not involve DSS. In this case, knockout mice lacking anti-inflammatory IL-10 were also observed to exhibit osteopenia and osteoporosis, confirming that the bone loss in DSS-treated mice is general to chronic inflammation and therefore, not likely a specific consequences of DSS exposure via some other physiologic route [Dresner-Pollak, et al., Gastroenterology 127:792 (2009)].

The balance between bone resorption by osteoclasts and bone formation by osteoblasts is regulated by several proteins produced by osteoblastic cells [reviewed in Ghishan and Kiela, Am. J. Physiol. Gastrointest. Liver Physiol. 300:G191 (2010); also see Ch. 2. In: Bone Health and Osteoporosis: A Report of the Surgeon General (2004) especially FIG. 2-6]. Osteoblastic production of Macrophage Colony Stimulating Factor (M-CSF) and Receptor Activated Nuclear Factor Kappa B Ligand (RANKL) stimulates development and activity of osteoclasts. Osteoblasts also produce osteoprotegerin (OPG), which functions as a soluble decoy receptor for RANKL and the local ratio of RANKL to OPG likely modulates osteoclast activity at sites of new bone synthesis. Production of RANKL is stimulated by a number of factors, including pro inflammatory cytokines such as IL-1, IL-6 and TNF-α, and RANKL is known to be activated in patients suffering from IBD [Franchimont, et al., Clin. Exp. Immunol. 138:491 (2004); Moschen, et al., Gut 54:479 (2005)]. Other factors, both known and unknown undoubtedly play important roles in balancing osteoclast and osteoblast activity and the disclosed invention is not limited by any specific model of regulation. The beneficial effects of the compositions and treatments disclosed here empirically improve bone status without regard to underlying theoretical molecular mechanisms.

Control of osteoblast and osteoclast activity by pro inflammatory cytokines and the association of bone disorders with IBD, suggests that interaction of the host immune system and gut microbiota may play a significant role in bone metabolism. Indeed, Sjogren and co-workers have found that germ free mice have significantly higher bone mass with a reduced number of osteoclasts relative to conventional mice raised under similar conditions [Sjogren, et al., Journal of Bone and Mineral Research 27:1357 (2012)]. Furthermore, these workers found that colonization of germ free mice with normal gut microbiota normalized bone mass and osteoclast numbers. Thus, it appears that interaction of the gut microbiota and host immune system can directly affect bone health.

Interaction between the gut microbiota and the immune system is to a large degree dependent on paracellular pathways, which are regulated by apical junctions between epithelial cells. Absent any pathologic condition, these junctions are not completely sealed but allow transport of water and solutes. These junctions are also the major route for the microbial sampling necessary to maintain immunogenic homeostasis. Loss of regulation of these junctions can result in changes in water flow, loss of coordinate solute transport and overstimulation of the immune system in response to increases in the level of microbial antigens. Such loss of regulation may be due to any number of factors, for example trauma or ulceration of intestinal epithelia may result in damage to the associated apical junctions. There is also growing evidence that certain hormonal changes in female subjects can alter regulation of apical junctions, not only in short term cycles in response to sex hormones such as estrogen and progesterone in the course of the esterous cycle, but also in response to the post menopausal cessation of such cycles [Braniste, et al., J. Physiol 587:3317 (2009)]. Similar long term alterations may occur in aging men as circulating estrogen levels decrease as a result of decreasing amounts of testosterone available for aromatization. Without being bound by theory, a method for restoring or preserving gut barrier function may improve bone health by mitigating the interaction of the gut microbiota and host immune system. Such an effect could serve to minimize unwanted stimulation of osteoclast activity and to promote osteogenesis.

In addition to modulating osteoclasts, osteoblasts actively engage in new bone formation. In this process of osteogenesis, osteoblasts lay down a protein matrix of Type I collagen and a noncollagenous protein, osteocalcin at the site of new bone synthesis. This protein matrix (the osteoid) is then mineralized with hydroxyapetite to form hard new bone [Ch. 2. In: Bone Health and Osteoporosis: A Report of the Surgeon General (2004)]. Osteocalcin, although largely localized to the osteoid, can be quantified in blood or urine samples and serves as a marker for active anabolic bone formation [Lian and Gundeberg, Clin. Orthop. Relat. Res. January(226):267 (1988)].

Currently, the only FDA-approved compound capable of stimulating new bone formation is parathyroid hormone (PTH), available commercially as Forteo® (teraperatide), a relatively expensive recombinant protein [Ch. 9. In: Bone Health and Osteoporosis: A Report of the Surgeon General (2004), p. 226]. To be effective, PTH needs to be administered by subcutaneous injection on a strict schedule to mimic the normal pulsatile action of the hormone on osteoblast differentiation [Dobnig and Turner, Endocrinology 138: 4607 (1997)]. PTH may not be compatible with bisphosphonate treatment, and therefore simultaneously increasing new bone synthesis with PTH while slowing bone resorption with bisposphonate treatment is problematic [Gasser, et al., J. Musculoskeletal Neuronal Interact. 1:53 (2000)]. In addition, PTH can potentially produce serious side effects such as kidney stones, anxiety and depression, and the duration of treatment is generally limited to no more than two years due to cancer risks. Thus, there is clearly a need for simple and robust new bone anabolic agents, especially agents capable of slowing bone resorption while promoting new bone synthesis.

In addition to bone health, the interaction of the gut microbiota and the immune system is implicated in a number of other aspects of animal welfare. Modern agricultural practices induce a great deal of stress which impacts growth, production, reproduction and disease susceptibly in farm animals [see J. C. Swanson, J. Animal Sci. 73:2744 (1995) for review]. The beneficial effect of antibiotic treatment in increasing growth yield and production of farm animals has long been recognized, but is highly controversial since it may produce a reservoir of antibiotic resistant bacteria which could compromise the medical efficacy of these drugs. The need for alternatives to antibiotics to promote growth and production of farm animals is well recognized and urgent.

SUMMARY

Interactions between the gut epithelium, endogenous bacteria and the animal immune system impact multiple aspects of animal physiology. HMW PEG provides a simple and robust way to enhance anabolic bone synthesis, while simultaneously lowering bone resorption. Other benefits of HMW PEG treatment include preventing, reducing, or ameliorating various disorders associated with chronic immunologic stimulation, whether due to infection, hormonal changes, injury, environmental stress or the exhaustion of metabolic precursors due to rapid growth. HMG-PEG provides a simple, safe and effective therapeutic and prophylactic in situations requiring long term treatment of chronic diseases (such as osteoperosis or irritable bowel disease), slow healing processes (bone formation after traumatic fracture) and in animal husbandry (improving the general health and yield of livestock).

The present invention satisfies at least one need in the art by providing a high molecular weight polyethylene glycol (HMW PEG) composition that provides effective protection against bone loss disorders. The present invention also provides uses of HMW PEG to reverse existing low bone mass and to improve various parameters of bone status such as bone mineral content, bone mineral density, bone volume fraction, trabecular number, thickness and spacing, and cortical area and marrow area. Also provided are uses of HMW PEG to improve osteogenesis and to reduce bone resorption. HMW PEG improves intestinal epithelial barrier function by an unknown mechanism, resulting in a reduction in concomitant bone loss associated with intestinal inflammation while at the same time increasing osteogenesis. Improvements in bone status occur whether inflammation is the direct result of pathologies of the bowel such as Crohn's disease or colitis, or indirectly as a result of changes in hormone levels that may compromise immunological integrity of the bowel. In the method, the HMW PEG compound may have an average molecular weight selected from the group consisting of at least 3,500 daltons, at least 5,000 daltons, at least 8,000 daltons, at least 12,000 daltons and at least 15,000 daltons. Also preferred are HMW PEG derivatives such as such as MDY-1001, having an average molecular weight between 15,000 and 20,000 daltons. A variety of structures of HMW PEG meeting the minimum average molecular weight criterion set forth above are contemplated, including a HMW PEG compound that comprises at least two hydrocarbon chains attached to a hydrophobic core, wherein each hydrocarbon chain has an average molecular weight of at least 40 percent of the HMW PEG compound, and wherein the hydrophobic core comprises a ring structure.

Similar compositions of HMW PEG have been described as effective agents for preventing or treating microbe mediated, radiation induced epithelial disorders in U.S. patent application Ser. No. 13/259,313, as well as therapeutic delivery systems for treatment of various epithelial diseases in U.S. patent application Ser. No. 11/578,388, both of which are incorporated herein by reference.

A therapeutically effective amount of HMW PEG will vary depending on known variables such as the age, weight, general health of the patient or animal subject, and a therapeutically effective amount is readily determinable using routine procedures, as would be known in the art. The method comprehends the administration of HMW PEG having the above-defined minimal average molecular weights, and comprehends an embodiment in which the HMW PEG having at least two hydrocarbon chains and a hydrophobic core, as described above, is administered. The method specifically comprehends treatment of subjects at risk for bone loss disorders.

Yet another aspect according to the disclosure is a method of protecting an animal from bone loss, comprising administering a prophylactically effective amount of a high molecular weight HMW PEG compound to an animal at risk of developing a bone loss disorder. Again, the HMW PEG compound may have an average molecular weight selected from the group consisting of at least 3,500 daltons, at least 5,000 daltons, at least 8,000 daltons, at least 12,000 daltons and at least 15,000 daltons. Also preferred are HMW PEG derivatives such as such as MDY-1001, having an average molecular weight between 15,000 and 20,000 daltons.

Still another aspect is a method of protecting an animal from bone loss, comprising administering a therapeutically effective amount of a high molecular weight HMW PEG compound to an animal currently suffering a bone loss disorder. The HMW PEG compound may have an average molecular weight selected from the group consisting of at least 3,500 daltons, at least 5,000 daltons, at least 8,000 daltons, at least 12,000 daltons and at least 15,000 daltons. Also preferred are HMW PEG derivatives such as such as MDY-1001, having an average molecular weight between 15,000 and 20,000 daltons.

Yet another aspect is drawn to a method of preventing bone loss in an animal, comprising administering a therapeutically effective amount of HMW PEG to the bowel of the animal. In some embodiments, the HMW PEG is administered prior to actual bone loss; in other embodiments, the HMW PEG is administered following detection of bone loss. In some embodiments, the HMW PEG is administered continuously or in a plurality of batches. Treatment with HMW PEG may consist of one or a limited number of administrations, or may involve a course of many separate administrations taking place over days, weeks, months or years.

Other aspects of the invention are drawn to methods of increasing growth performance of an animal. Growth performance may mean an increase in growth rate, decrease in lean muscle mass, or increases in production of desired animal products such as milk in the case of dairy cows, eggs in the case of chickens (layers) or meat as in the case of beef cattle, pigs, sheep, chickens (including but not limited to broilers and fryers), turkeys, ducks and other domesticated meat animals.

Yet another aspect is drawn to a method of decreasing the frequency and severity of diarrheal disease in humans and other animals. Such diarrheal diseases include both inflammatory and non-inflammatory diarrhea such as that caused by inflammatory bowel disease, food poisoning, infection, or environmental stress. Infections may be the result of bacterial or parasitic invasion. Environmental stressors include any conditions such as crowding, confinement or physical handling of an animal that directly or indirectly affect the immune status of the animal.

In each of the foregoing aspects according to the disclosure, the HMW PEG may be administered by any route known in the art, such as enteric administration or parenteric administration. More particularly, any of the foregoing methods may involve HMW PEG administration orally, by gastric feeding tube, by duodenal feeding tube, by gastrostomy, by enema, by gastric lavage, by colonic lavage, by direct injection into the gastrointestinal tract or by surgical infusion. Also, in each of the foregoing aspects according to the disclosure the HMW PEG may have at least two hydrocarbon chains wherein each chain has an average molecular weight of at least 40 percent of the HMW PEG compound, and a hydrophobic core, wherein the hydrophobic core may include one or more aromatic or non-aromatic rings.

An additional aspect of the invention provides a kit comprising packaging material, an effective amount of HMW PEG and means for delivery, wherein the packaging material comprises a label or package insert indicating the HMW PEG can be used for treating, ameliorating, or preventing a condition characterized as a bone loss disorder.

Other features and advantages of the present invention will be better understood by reference to the following detailed description, including the drawing and the examples.

Comparison of control and OVX sample groups shows a statistically significant reduction in bone mineral content due to post menopausal bone loss. Comparison of the HMW PEG-treated sample groups to their untreated companions shows these animals benefitted from higher levels of trabelcular bone mineral content as a consequence of HMW PEG treatment.

Figure 3:
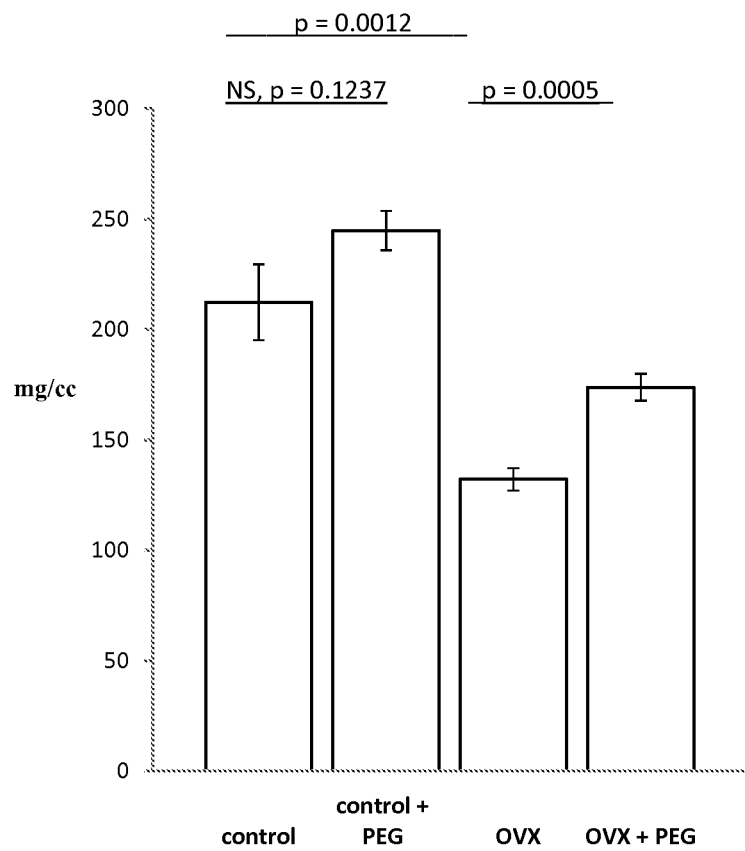

FIG. 3 represents relative trabecular bone mineral density (mg/cc) in control, control+PEG, OVX and OVX+PEG mice. Comparison of control and OVX sample groups shows a statistically significant reduction in bone mineral content due to post menopausal bone loss. Treatment of the OVX animals with HMW PEG resulted in a statistically significant improvement in trabecular bone mineral density (compare OVX and OVX+PEG). Likewise, HMW PEG treatment appears to have improved trabecular bone mineral density of the control animals as well, although the effect is less pronounced and not as statistically certain.

Figure 4:
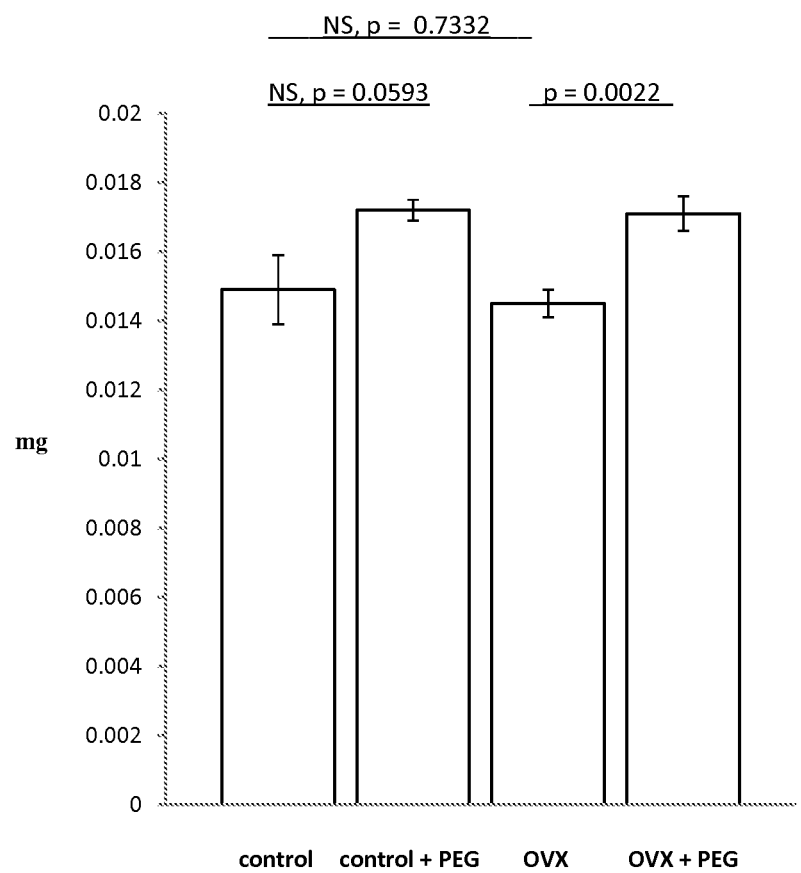

FIG. 4 represents relative cortical bone mineral content (mg) in control, control+PEG, OVX and OVX+PEG mice. There is little difference between control and OVX animals, indicating that cortical bone may be less sensitive to the post menopausal effects on bone loss. However, treatment with HMW PEG increases cortical bone mineral content in both healthy and post menopausal animals.

Figure 5:
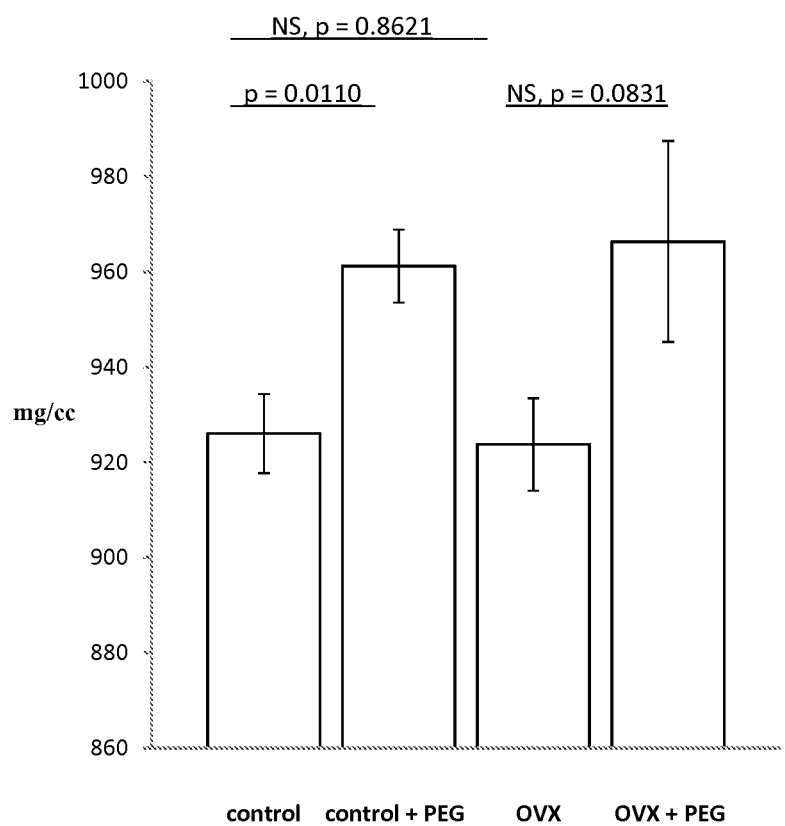

FIG. 5 represents relative cortical bone mineral density (mg/cc) in control, control+PEG, OVX and OVX+PEG mice. As in FIG. 4, there is little difference between control and OVX animals, yet there is distinct improvement upon treatment with HMW PEG in both healthy and post menopausal animals.

Figure 6:
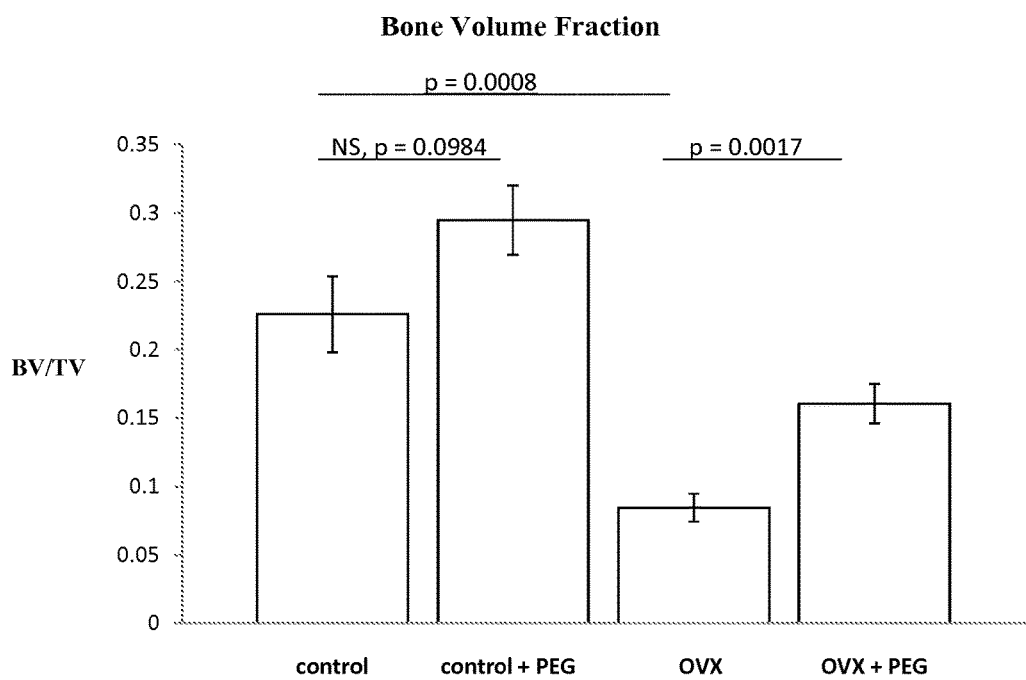

FIG. 6 represents relative bone volume fraction (BV/TV) in control, control+PEG, OVX and OVX+PEG mice. Comparison of control and OVX sample groups shows a statistically significant reduction in bone volume fraction due to post menopausal bone loss. Treatment with HMW PEG provides a large and statistically significant improvement in bone volume fraction in animals suffering from post menopausal bone loss Improvement in healthy animals treated with HMW PEG also occurs, although less dramatically and with a much lower level of certainty.

Figure 7:
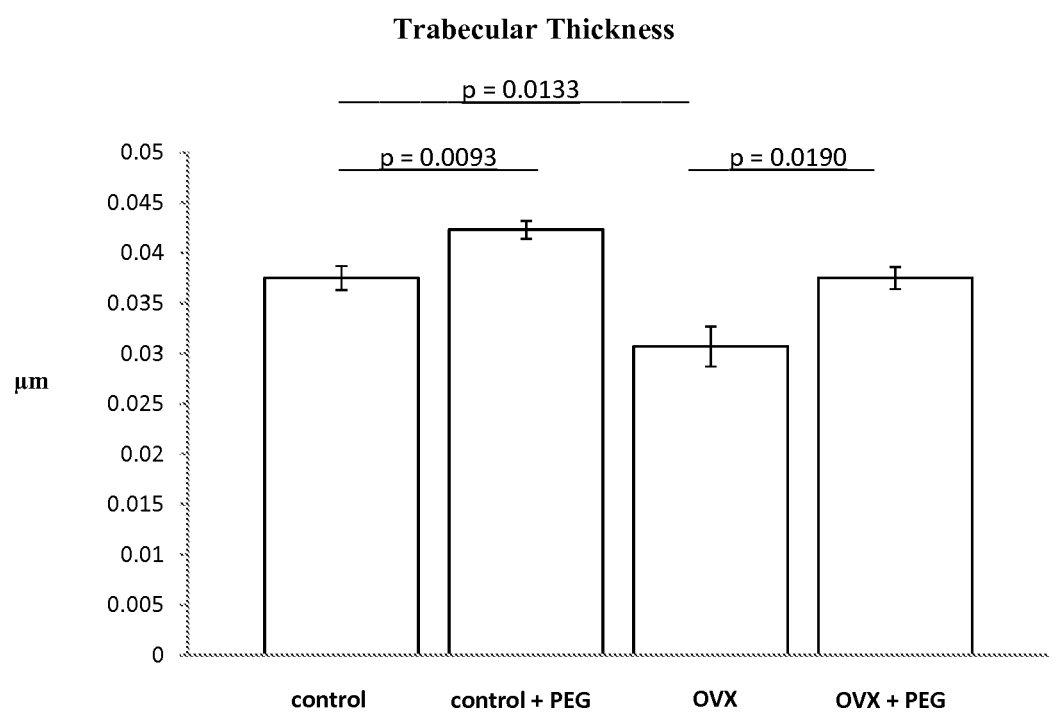

FIG. 7 represents relative trabecular thickness (μm) in control, control+PEG, OVX and OVX+PEG mice. Post menopausal bone loss is reflected in the reduction of the average trabecular thickness in the OVX animals relative to the control group animals. Both healthy animals and animals suffering from post menopausal bone loss benefit from HMW PEG treatment, with the post menopausal animals restored to almost the same level of average trabecular thickness as healthy animals.

Figure 8:
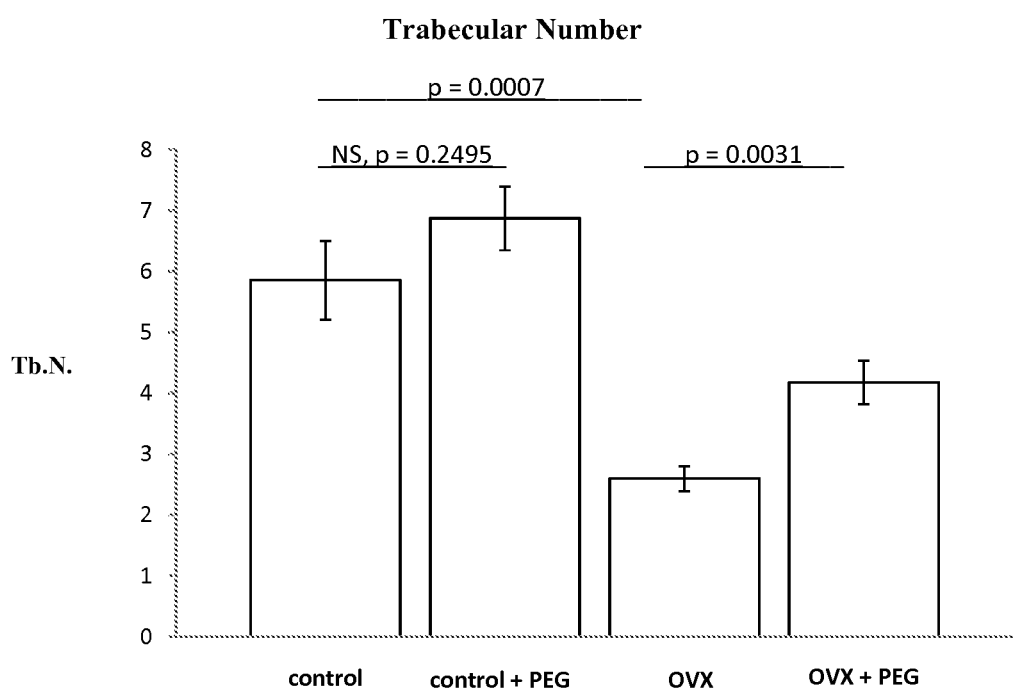

FIG. 8 represents trabecular number (Tb.N.) in control, control+PEG, OVX and OVX+PEG mice. Post menopausal bone loss is also reflected in the reduction of the average trabecular number in the OVX animals, relative to the control group animals. HMW PEG treatment of post menopausal animals significantly improves trabecular number, whereas treatment with HMW PEG seems to impart some benefit to otherwise healthy animals, but not as significantly.

Figure 9:
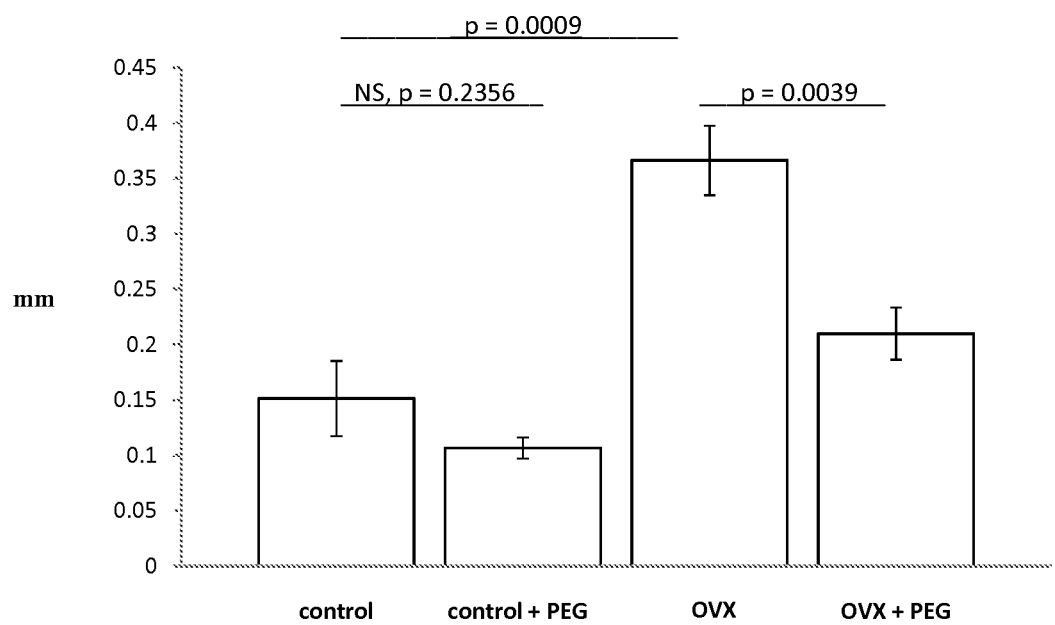

FIG. 9 represents trabecular spacing (mm) in control, control+PEG, OVX and OVX+PEG mice. The difference in trabecular spacing due to post menopausal bone loss is apparent by comparing the control group animals with the OVX group. Treatment with HMW PEG significantly decreases trabecular spacing in OVX animals to almost the same level as observed in healthy animals. Less significantly, treatment with HMW PEG also appears to reduce trabecular spacing in healthy animals.

Figure 10:
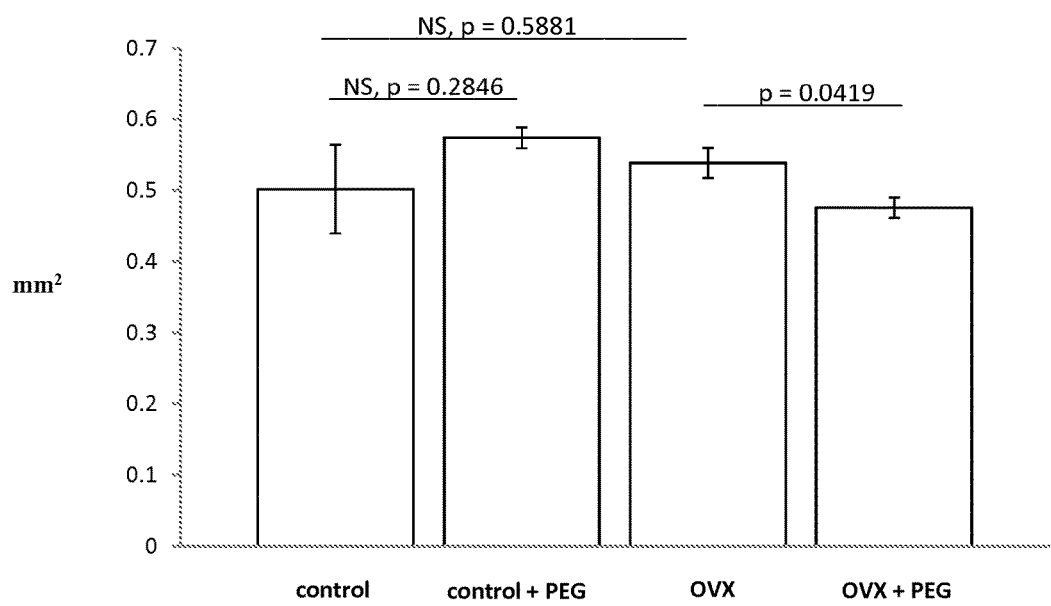

FIG. 10 represents cortical marrow area (mm$^2$) in control, control+PEG, OVX and OVX+PEG mice. There is little apparent difference between healthy animals and the post menopausal animals in cortical marrow area. Likewise, there is little significant change in healthy animals treated with HMW PEG. There is a significant decrease in cortical bone marrow area in the post menopausal animals treated with HMW PEG, suggesting accumulation of new bone at the expense of cortical marrow area.

Figure 11:
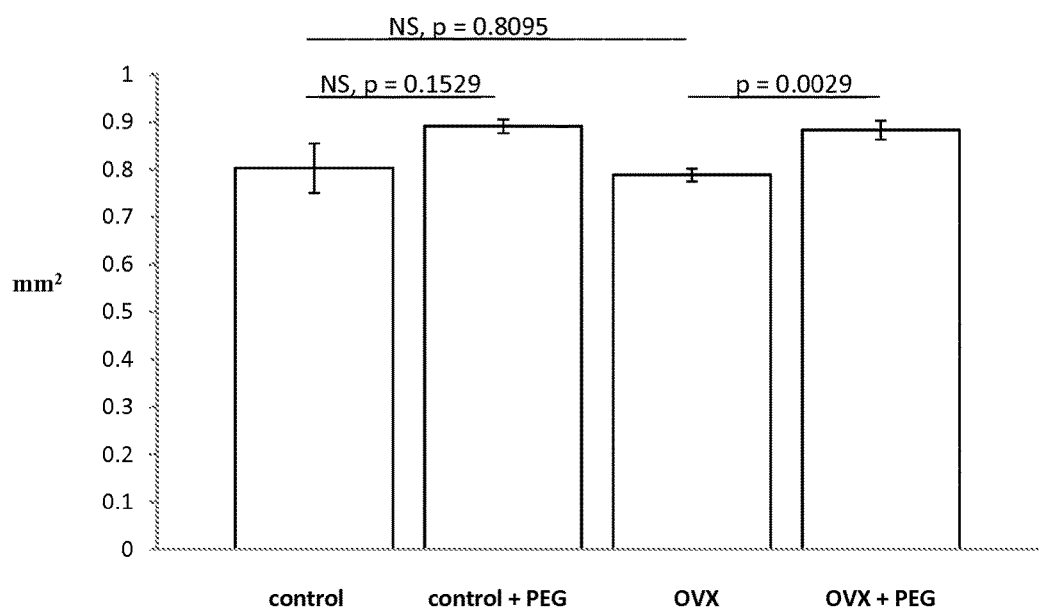

FIG. 11 represents cortical area (mm$^2$) in control, control+ PEG, OVX and OVX+PEG mice. The cortical area profiles of healthy and post menopausal animal groups treated with HMW PEG are consistent with the cortical marrow area pattern in FIG. 10. There is little significant difference between healthy and post menopausal animals, but treatment with HMW PEG increases cortical bone area if only slightly, indicating accumulation of new bone.

Figure 12:
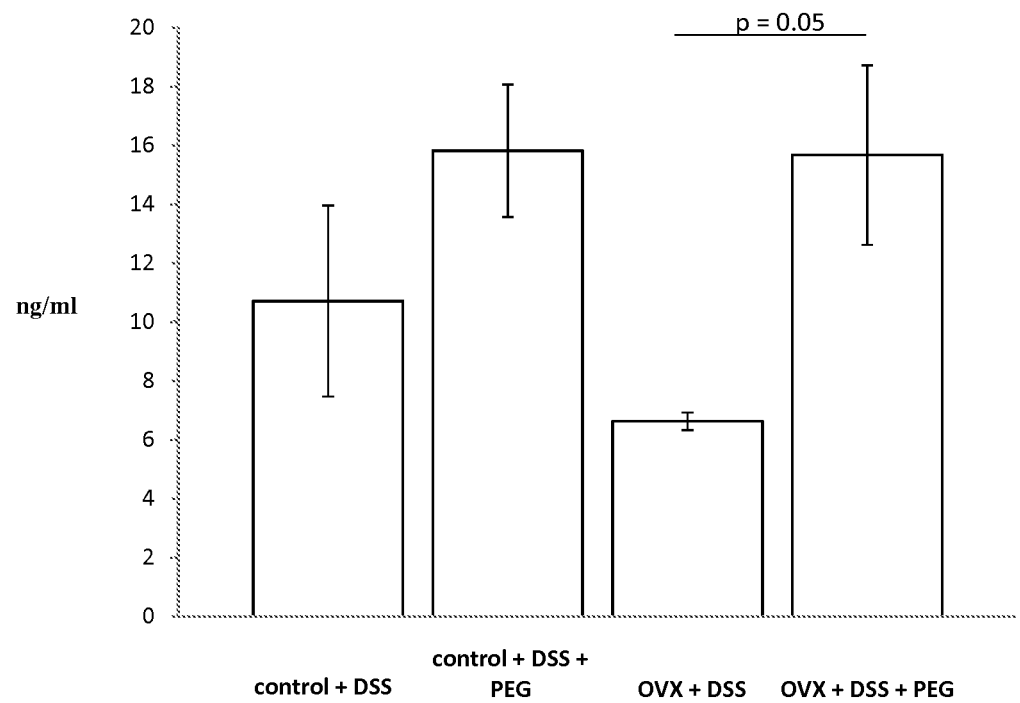

FIG. 12 represents relative serum osteocalcin concentration (ng/ml) in OVX, OVX+PEG, OVX+DSS and OVX+ DSS+PEG mice. Comparison of the control+DSS group with the OVX+DSS animals shows that even in animals suffering from DSS induced IBD, there is an additional post menopausal (OVX) bone loss effect. Treatment with HMW PEG significantly increases the level of serum osteocalcin, which as a marker of osteogenesis, indicates that new bone synthesis is increased in animals at risk from both IBD and post menopausal bone loss. An improvement in animals suffering IBD treated with HMW PEG is also apparent, though with less statistical certainty. Significantly, treatment with HMW PEG appears to increase this marker of anabolic new bone synthesis in both groups of animals to the same level.

Figure 13:
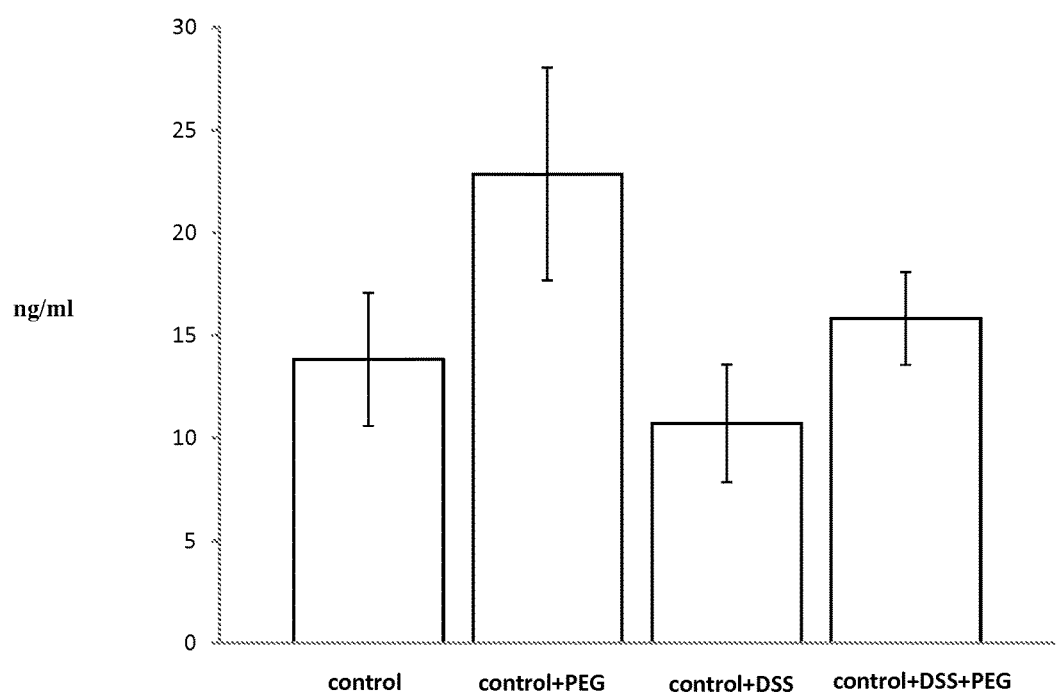

FIG. 13 represents relative serum osteocalcin concentration in (ng/ml) in control, control+PEG, control+DSS and control+DSS+PEG mice. Comparison of healthy animals with animals suffering IBD bone loss (control versus control+DSS) suggests that the IBD animals may have lower levels of new bone synthesis (osteogenesis), consistent with previously published reports [Harris, et al., (2009)]. Treatment with HMW PEG of both healthy animals and IBD animals (control+PEG and control+DSS+PEG) increases serum osteocalcin levels suggesting that such treatment increases osteogenesis. Comparison of the healthy animals with the HMW PEG treated IBD animal group shows that treatment with HMW PEG restores osteogenesis in IBD animals to the same level as that found in healthy animals.

Figure 14:
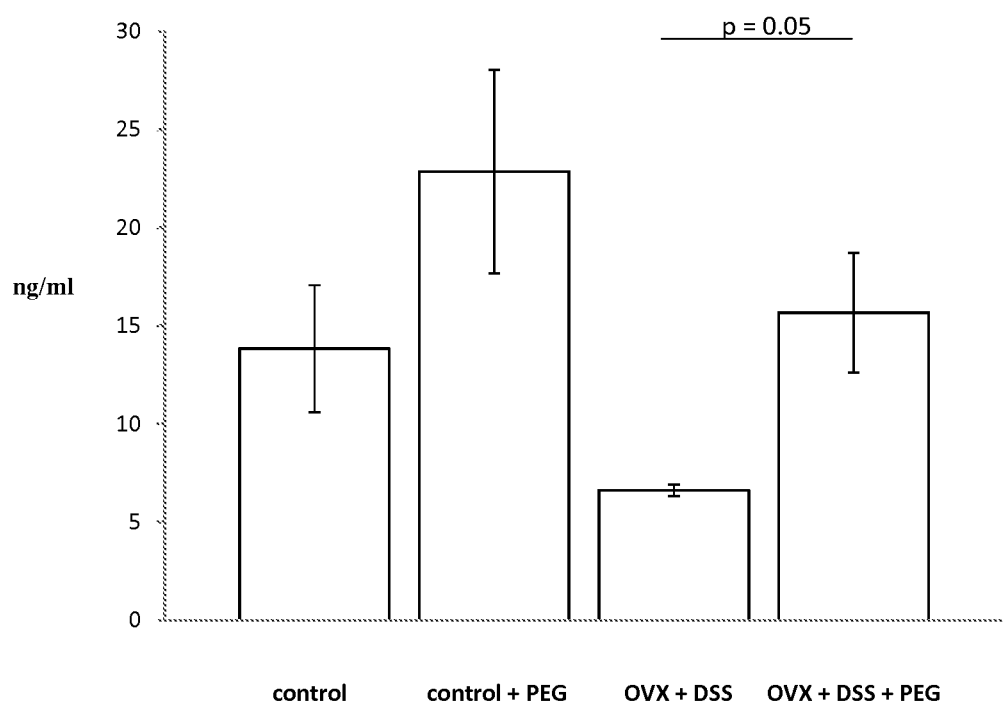

FIG. 14 represents relative serum osteocalcin concentrations in control, control+PEG, OVX+DSS and OVX+DSS+PEG mice. Comparison of healthy animals with animals suffering both IBD and post menopausal bone loss (control versus OVX+DSS) indicates that the IBD and post menopausal animals have significantly lower levels of bone synthesis, consistent with post menopausal bone loss reducing new bone synthesis in addition to bone loss due to IBD. Comparison of healthy animals with animals suffering IBD and post menopausal bone loss (control+PEG versus OVX+DSS+PEG) group shows that treatment with HMW PEG restores osteogenesis of animals at risk for IBD and post menopausal bone loss to the same level as that found in healthy animals.

Figure 15:
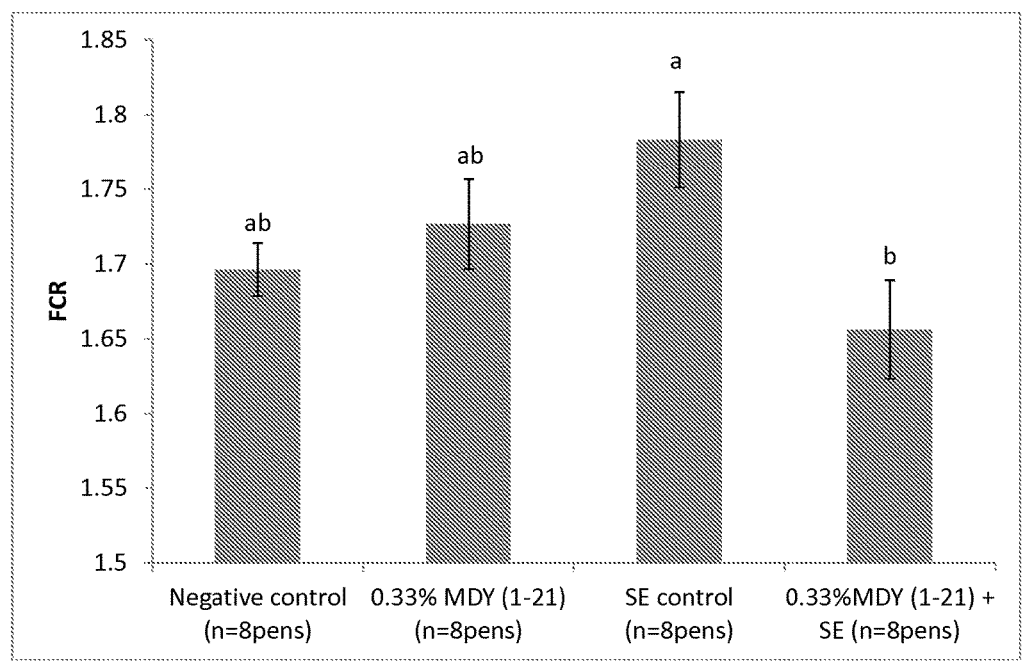

FIG. 15 depicts the feed conversion rate (FCR) of healthy and infected broiler chickens. The birds in this study were segregated into multiple pens (15 birds per pen) and treated as four experimental groups (8 pens per group). The negative control group comprised healthy birds receiving no special treatment. The 0.33% MDY(1-21) group represents birds treated with the HMW PEG MDY-1001. Birds in the SE control group were infected with *Salmonella Enteritidis*, but received no other special treatment. Birds in the 0.33% MDY(1-21)+SE group were infected with *Salmonella Enteriditis* and were treated with HMW PEG. The FCR is determined by dividing the body weight gain of each pen within the group by the total feed consumed by each pen within the group assessed at twenty days.

Figure 16:
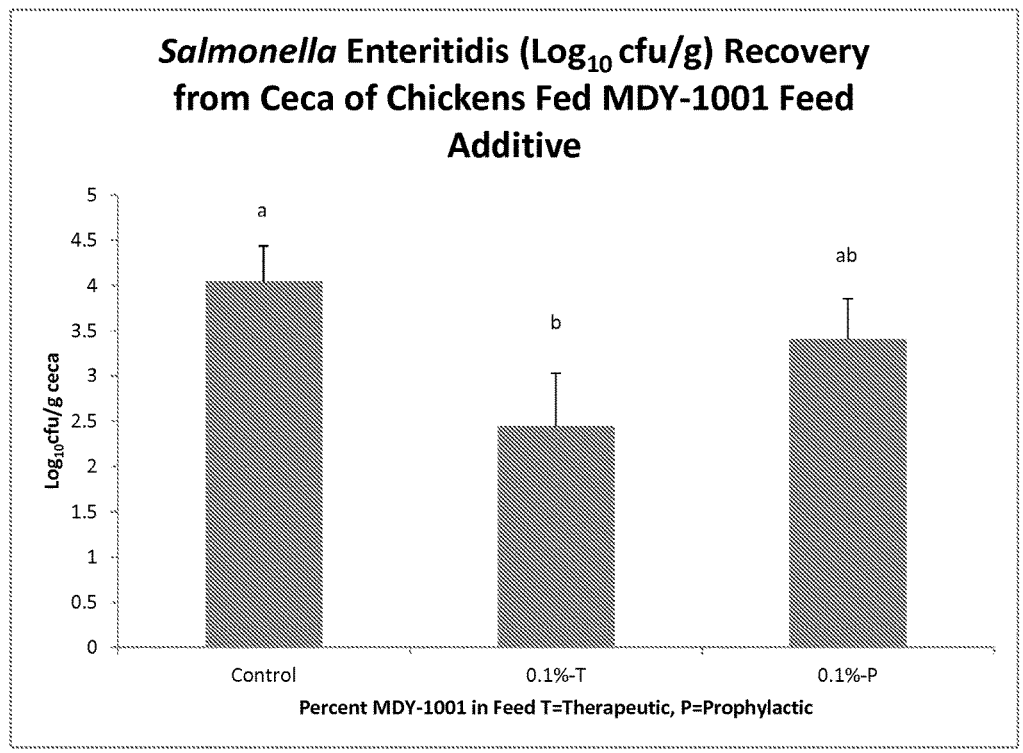

FIG. 16 reports the effect of HMW PEG on recovery of bacteria from infected broiler chickens. All birds in this study were infected with *Salmonella Entiriditis* and the amount of *S. Enteriditis* present in the cecum of each bird was determined at the end of the treatment period. Birds in the control group received no special treatment. Birds in the 0.1%-T group were treated with HMW PEG MDY-1001. Birds in the 0.1%-P group were treated with a common poultry prophylactic. The cecum of each chicken was removed and weighed and the number of colony forming units of *S. Enteriditis* recovered from each cecum determined by standard microbiological methods.

DETAILED DESCRIPTION

The present invention provides methods for treating bone loss disorders and conditions associated with bone loss. The present invention is based on the discovery that administration of a composition comprising high molecular weight polyethylene glycol (HMW PEG) to animals with low bone density and physiologic bone profiles characteristic of osteoporosis or osteopenia causes an increase in bone mass and density concomitant with improvement in trabecular and cortical bone profiles. Administration of HMW PEG not only decreases bone resorption, but also increases osteogenesis, as shown by increasing serum osteocalcin levels. Thus, compositions comprising HMW PEG are surprisingly useful in treating bone loss and associated disorders. The discovery is unexpected in view of the efficacy of the treatment for bone loss disorders caused by conditions not directly related to gastrointestinal health, such as hormonal changes in bone health resulting from post-menopausal osteoporosis. Furthermore, treatment with HMW PEG also improves various parameters of bone health in a healthy animal lacking any disorder directly or indirectly affecting gastrointestinal health.

In addition to treating bone loss and associated disorders, administration of HMW PEG can improve bone repair in humans and other animals with normal bone profiles who may have suffered an injury requiring new bone to heal, such as a break or stress fracture.

Treatment with HMW PEG will also improve bone integrity in animals experiencing other forms of stress related to physiologic bone formation. For example, soft bone disease in chickens occurs in production layers as a consequence of depletion of vitamin D, calcium or other factors involved in egg shell formation. Likewise, domesticated turkeys and chickens (including but not limited to broilers and fryers) frequently suffer bone diseases such as bacterial necrosis of the femur head (osteomyelitis complex) due to infection, and failure of the tibial cartilage to ossify (tibial dyschondroplasia) as a consequence of the fast growth rates of production strains. Larger animals are also susceptible to bone damage, especially those bred for high reproductive capacity, fast growth rates, and those raised in close quarters. For example, pigs suffer osteomalacia as a result of high lactation demand on breeding sows, metabolic bone diseases such as rickets, and non-metabolic bone diseases due to infection as a consequence of stress and contamination with fecal matter in high density swine production facilities.

Growth performance of animals treated with HMW PEG is also improved. Growth performance may mean improved production of milk in the case of dairy cattle, or eggs in the case of chickens (layers) as well as improvement in production of lean muscle mass in the case of animals raised for meat production. Growth performance provides a general assessment of the overall health of an individual animal and bone disorders always negatively impact the overall health of an organism. Regardless of whether a bone disorder as a consequence of disruptions to gastrointestinal health is manifest, treatment with HMW PEG has been found to improve growth performance of treated animals.

"Animal" is given its conventional meaning of a non-plant, non-protist living being. A preferred animal is a vertebrate animal, such as a mammal, a fowl or a fish. Preferred mammals include but are not limited to, humans as well as domesticated mammals such as cattle, pigs, sheep, horses, dogs, or cats. Preferred fowl include but are not limited to domesticated fowl, such as chickens, turkeys and ducks. Preferred fish include but are not limited to farmable fish such as salmon, tilapia, catfish, grouper, seabeam and seabass.

It is understood that the term "bone loss disorder" relates to conditions such as osteoporosis or osteopenia as defined by The Surgeon General [Ch. 3. In: Bone Health and Osteoporosis: A Report of the Surgeon General (2004)] or the World Health Organization [WHO Scientific Group on the Burden of Musculoskeletal Conditions at the Start of the New Millennium. The burden of musculoskeletal conditions at the start of the new millennium: Report of a scientific group. Geneva, Switzerland: World Health Organization technical report series 919; 2003, p. 27]. Operationally, osteoporosis is defined by these authorities as a bone mineral density (BMD) of less than 2.5 standard deviations below the mean average BMD of young adult women (BMD T-score <−2.5). Osteopenia is operationally defined as a BMD 1 to 2.5 standard deviations below the mean average BMD of young adult women (−2.5<BMD T-score>−1.0). Clinically, osteoporosis is usually recognized by characteristic low trauma fractures to the wrist, vertebrae and hip. In addition, as used here "bone loss disorder" also refers to conditions in which physical bone characteristics other than BMD indicate that significant bone loss has occurred. For example, reduced bone mineral content, reduced bone volume fraction, reductions in trabecular thickness and trabecular number, increases in trabecular spacing, increases in cortical marrow area or decreasing cortical bone area may all indicate a progression to osteopenia or osteoporosis. It is also understood that where the term "bone loss disorder" is used here it refers to any pathology resulting in a decrease in bone quality by any of these indicators of bone loss.

Only certain HMW PEG formulations are likely to be effective for improving growth performance or treating bone loss disorder. Compositions of polyethylene glycol (PEG) are commonly used to purge bowel contents prior to colonoscopy or surgical procedures involving the gastrointestinal tract. In general, forms of PEG used for bowel cleansing have molecular weights of 3.350 kilodaltons or less (e.g. MiraLAX® or MoviPrep®), which is substantially shorter than the HMW PEG compositions provided by the present invention. Further, the strong laxative effect of these lower molecular weight PEG formulations makes them unsuitable for long term application as a therapeutic treatment. In addition, Alverdy and co-workers reported that administration of HMW PEG provides significant protection against radiation induced sepsis in mice, while PEG of 3.35 kilodaltons provided little or no protection [Valuckaite, et al., Am. J. Physiol. Gastrointest. Liver Physiol. 297:G1041 (2009); U.S. patent application Ser. No. 11/578,388]. These results indicate a qualitative difference in interactions between gut epithelia and HMW PEG and gut epithelia and lower molecular weight PEG compounds. The present invention discloses that interaction of HMW PEG with gut epithelia also reduces bone loss in animals at risk of a bone loss disorder.

"HMW PEG" refers to relatively high molecular weight PEG defined as having an average molecular weight greater than 3.5 kilodaltons. Preferably, HMW PEG has an average molecular weight greater than 1 kilodalton and, in particular embodiments, HMW PEG has an average molecular weight that is at least 5 kilodaltons, at least 8 kilodaltons, at least 12 kilodaltons, at least 15 kilodaltons, and between 15 and 20 kilodaltons (MDY-1001). In one embodiment, the HMW PEG has at least two hydrocarbon chains, with each chain having an average molecular weight of at least 40 percent of the HMW PEG and a hydrophobic core with that core having a ring structure, such as 1-4 rings with each ring having 5 or 6 ring carbons and including, but not being limited to, aromatic rings.

Additionally, "HMW PEG" compounds include HMW PEG derivatives wherein each such derivative compound contains an HMW PEG compound as a moiety to which is attached at least one additional functional group. Thus, "HMW PEG" compounds include underivatized HMW PEG compounds and HMW PEG derivative compounds. Preferred HMW PEG derivatives are cationic polymers. This definition of an "HMW PEG" compound avoids the confusion in characterizing molecules such as the molecule of the preferred embodiment disclosed in the preceding paragraph, wherein an "HMW PEG" compound comprising at least two hydrocarbon chains and a hydrophobic core can be termed an HMW PEG compound or an HMW PEG derivative compound depending on one's perspective. As defined herein, such a molecule is an HMW PEG compound, regardless of whether it is regarded as derivatized or not. Exemplary functional groups include any of the alkoxy series, preferably C1 (methoxy) to C10 (caproxy), any of the aryloxy series, phenyl and substituted phenyl groups. Such functional groups may be attached at any point to an HMW PEG molecule, including at either terminus or in the middle; also included are functional groups, e.g., phenyl and its substituents, that serve to link to smaller PEG molecules or derivatives thereof into a single HMW PEG-like compound. Further, the HMW PEG-like molecules having an additional functional group may have one such group or more than one such group; each molecule may also have a mixture of additional functional groups, provided such molecules are useful in treating, ameliorating or preventing a disease, disorder or condition or in stabilizing at least one therapeutic during delivery thereof.

"Formulation" means a composition suitable for therapeutic administration to a living animal, such as a human patient. Preferred formulations according to the invention comprise a solution balanced in viscosity, electrolyte profile and osmolality, comprising an electrolyte and HMW PEG.

In one embodiment of the present invention, administration of a composition comprising an effective amount of HMW PEG is used to treat bone loss disorder in a subject in need of such treatment. In another embodiment, administration of a composition comprising an effective amount of HMW PEG is used to increase growth performance of an animal.

"Administration" means introduction of the therapeutic material into the gastrointestinal tract of an animal or human patient. Introduction of the therapeutic material may be oral, or rectal, or enteral by direct injection or surgical irrigation. A device such as a feeding tube, duodenal tube, enema or colon tube may be used as a means of administering HMW PEG.

An "effective amount" or "effective dose" is that amount of a substance that provides a beneficial effect on the organism receiving the dose and may vary depending upon the size and condition of the organism receiving the dose and other variables recognized in the art as relevant to a determination of an effective dose. The process of determining an effective amount involves routine optimization procedures that are within the skill in the art.

In one aspect of the invention HMW PEG is administered to an animal with an abnormal condition at risk for developing a bone loss disorder to ameliorate bone loss by slowing the rate of bone resorption and increasing the rate of osteogenesis.

An "abnormal condition" is broadly defined to include animal diseases, animal disorders and any abnormal state of animal health that is characterized by a risk of developing a gastrointestinal or bone loss disorder.

"Ameliorate" means reducing the degree or severity of, consistent with its ordinary and accustomed meaning.

"Osteogenesis" is understood to refer to anabolic new bone synthesis.

In one aspect of the invention HMW PEG is administered to an animal suffering from inflammatory bowel disease to ameliorate bone loss or to restore bone health.

"Inflammatory bowel disease" describes a spectrum of intestinal ailments, including Crohn's disease, which can occur anywhere in the gastrointestinal tract, and ulcerative colitis, which is primarily localized to the colon and large intestine. Other conditions resulting in chronic or episodic inflammation of the bowel also constitute inflammatory bowel disease regardless of specific or idiopathic origin.

In another aspect of the invention HMW PEG is administered to an animal suffering from bone loss due to menopause or andropause to ameliorate such bone loss or restore bone health.

"Menopause" as used here refers to decreases in the level of circulating estrogen and progesterone due to aging, disease, trauma, or to surgical removal of both ovaries, referred to here as overiectomy, but also commonly known as oophorectomy.

"Andropause" as used here refers to decreases in circulating testosterone levels due to aging, disease, trauma or to surgical removal of both testes.

"Bacterial burden" means the amount of recoverable bacteria from an animal. Bacterial burden is a measure of the ability of an animal to shed bacteria into its environment and potentially contaminate other animals in its immediate vicinity. Under conditions of close confinement a single infected animal with high bacterial burden can more easily transmit the infection than one with low bacterial burden. The ability of HMW PEG to reduce bacterial burden is an important factor in improving growth performance.

A related aspect of the invention is a kit for administering HMW PEG, comprising an effective dose of HMW PEG, means for administering the effective dose and a protocol describing use of the HMW PEG and how it is to be administered. Suitable protocols include any of the methods disclosed herein or known in the art relating to the administration, delivery or application of HMW PEG. In some embodiments of this aspect of the invention, the kit further comprises additional therapeutic compounds.

In a preferred embodiment of the present invention, a composition comprising an effective amount of HMW PEG further comprising anti-inflammatory, other immune system modulators, an antibiotic, an anti-cancer agent, an anti-ulcer agent, a growth factor, a cytokine, bisphosphonates, a protein hormone and mixtures thereof. Exemplary therapeutics include a 5-amino salicylate, a compound comprising a 5-amino salicylate moiety, a corticosteroid, methotrexate, 6-mercaptopurine, cyclosporine, vancomycin, metronidazole, a cephalosporin, taxane, a compound comprising a taxane moiety, camptothecin, a compound comprising a camptothecin moiety, 5-fluorouracil, a compound comprising a 5-fluorouracil moiety, an anti-androgen compound, an anti-estrogen compound, alendronate, risedronate, an epidermal growth factor, intestinal trefoil factor, insulin, somatostatin, teriparatide, an interferon and mixtures thereof. In some embodiments, the therapeutic is a probiotic bacterium, or a compound or composition derived from a probiotic bacterium.

The following examples illustrate embodiments of the invention. Example 1 describes the improvements in various parameters of bone health by HMW PEG in a post-menopausal osteoporosis mouse model. Example 2 describes HMW PEG improvement of a marker for anabolic bone synthesis in an IBS induced osteoporosis mouse model. Example 3 describes improvement of anabolic bone synthesis in a healthy subject group not suffering from any bone loss disorder upon treatment with HMW PEG. Example 4 describes use of HMW PEG to improve the metabolic efficiency of chickens infected with enteric pathogens. Example 5 describes use of HMW PEG to reduce the burden of pathogenic bacteria in infected chickens. Example 6 demonstrates the use of HMW PEG to improve weight gain and reduce gastrointestinal distress in piglets raised under mock production conditions.

EXAMPLES

The following Examples are meant to be illustrative of the invention and are not intended to limit the scope of the invention as set out in the appended claims.

Example 1

Twenty-four young female BALB/c mice were obtained from Jackson Laboratories (The Jackson Laboratory, Bar Harbor, Me.). The mice were divided into two equal cohorts and the mice in one cohort overiectomized at ten weeks of age. Each cohort was further subdivided into two groups of six overectimized (OVX) mice and two groups of six fertile mice. One group of OVX and one group of fertile mice received PEG through gavage (3× per week with 2 g/kg body weight HMW PEG). Throughout the course of the work reported here, the HMW PEG formulation was MDY-1001, which is comprised of 10% HMW PEG of average 15K MW, and up to 2% higher molecular weights of PEG with the remainder 8K MW PEG.

These animals also received 1% HMW PEG in 5% dextrose in water (D5W), provided ad libitum to maintain an effective amount of HMW PEG between gavage treatments. The other two groups were gavaged with equivalent volumes of water on the same schedule and provided with D5W. This resulted in four groups, a control group of fertile mice unexposed to PEG (control), a group of fertile mice exposed to PEG (control+PEG), a group of OVX mice unexposed to PEG (OVX), and a group of OVX mice exposed to PEG (OVX+PEG). Throughout the experiment animals were given standard chow and water ad libitum and were maintained on a 12 hour light/dark cycle. All animal procedures were approved by the Michigan State University Institutional Animal Care and Use Committee.

Animals were harvested at 14 weeks of age. Blood was sterilely collected at the time of harvest by cardiac puncture, allowed to clot at room temperature for 5 minutes and then centrifuged at 4,000 rpm for 10 minutes. Serum was removed, frozen in liquid nitrogen and stored at −80° C. Femurs were also removed and processed as described below.

1. MicroComputed Tomography of HMW PEG Treated Fertile and OVX Mice.

Bone structure was analyzed via microcomputed tomography (μCT). Femurs (fixed in 10% buffered formalin for 24 hours and then maintained in 70% ethanol) were scanned using a GE Explore Locus μCT system at a voxel resolution of 20 μm obtained from 720 views. Beam angle of increment was 0.5, and beam strength was set at 80 peak kV and 450 μA. Integration time for each scan was 2000 ms. Each run consisted of bones from each group and a calibration phantom to standardize grayscale values and maintain consistency. On the basis of autothreshold and isosurface analyses of multiple bone samples, a fixed threshold (835) was used to separate bone from bone marrow. Accuracy was verified by comparison of the original and segmented image slices. Bone analyses were done blind to the condition of the bones. Trabecular bone analyses were performed in a region of trabecular bone defined at ~0.15 mm (~1% total length) distal to the growth plate of the proximal femur extending 1.5 mm (10% bone length) toward the diaphysis excluding the outer cortical bone. Trabecular bone mineral content, bone mineral density, bone volume fraction, thickness, spacing, and number values were computed by the GE Healthcare MicroView software application for visualization and analysis of volumetric image data. Cortical measurements were performed in a 2×2×2 mm cube centered midway down the length of the bone using a threshold of 1430 to separate bone from marrow.

Figure 1:
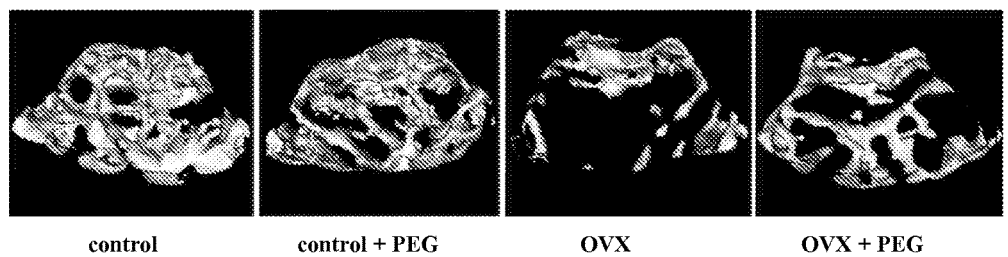
FIG. 1 is a graphic visualization of representative μCT scans of femurs from untreated (control) mice, control mice treated with HMW PEG (control+PEG), overiectomized (OVX) mice and OVX mice treated with HMW PEG (OVX+PEG). Comparison of the control panel with the OVX panel illustrates the extent of post menopausal bone loss resulting from overiectomy. Comparison of the OVX panel with the OVX+PEG panel illustrates the ameliorative effect treatment with HMW PEG has on post menopausal bone loss. Comparison of the control+PEG panel with the control panel indicates that even animals lacking an underlying bone loss disorder may derive some benefit in bone status from treatment with HMW PEG.

Four representative µCT images of trabecular bone from each group are shown in FIG. 1. The panel marked "control" represents the bone structure of a normal untreated mouse, whereas the panel marked "OVX" shows the equivalent bone structure in a mouse experiencing post menopausal osteoporosis. The panel marked "control+PEG" depicts the bone structure of a mouse treated with HMW PEG. Comparison of this panel with the control panel indicates a relative increase in the amount of bone. The panel marked "OVX+PEG" depicts the bone structure that occurs in a mouse suffering post-menopausal osteoporosis treated with HMW PEG. Comparison with the OVX panel reveals a very obvious increase in the amount of bone. These data indicate that treatment with HMW PEG can increase the amount of bone present in subjects suffering post-menopausal osteoporosis.

2. Trabecular Bone Mineral Content of HMW PEG Treated Fertile and OVX Mice.

Figure 2:
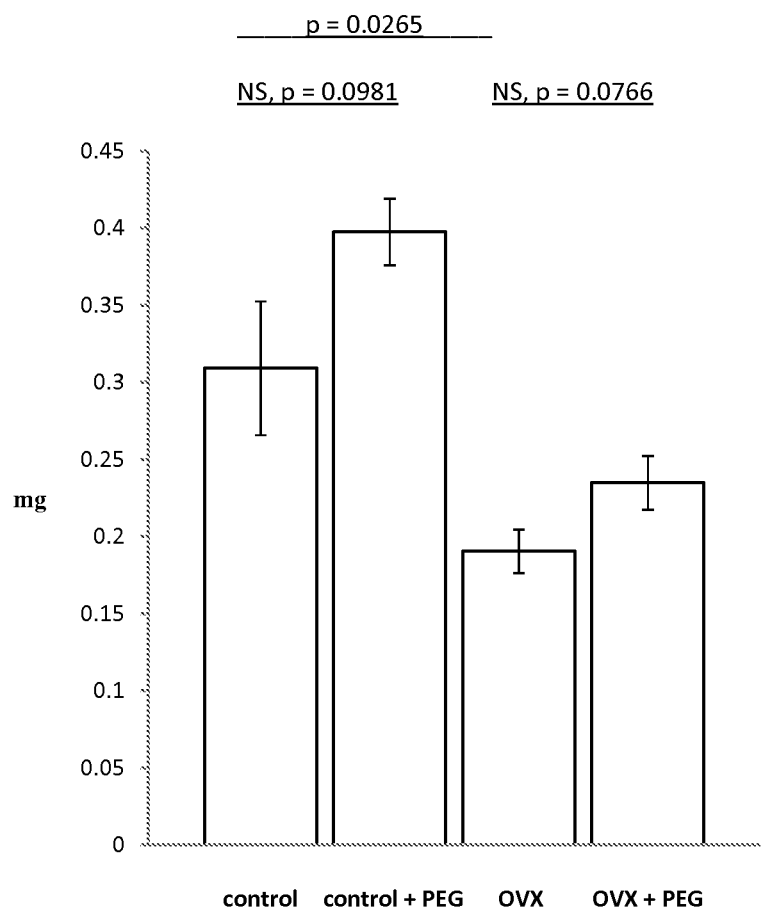
FIG. 2 represents relative trabecular bone mineral content (mg) in control, control+PEG, OVX and OVX+PEG mice. In this and all subsequent plots, standard deviation within each subject group is shown as vertical error bars. Horizontal bars indicate statistical quality between subject groups asp value derived from Student's t-test. NS denotes $p>0.05$, considered here as a non-statistically significant result.

Trabecular bone mineral content (BMC) is representative of the amount of bone mineral present across a given region of trabecular bone. BMC is known to decrease in women who have had both ovaries removed, and this is reflected in the OVX mouse model shown in FIG. 2. Comparison of the OVX sample group with the control group shows a statistically significant (p=0.0265) average decrease in BMC of almost 62%. This closely parallels the extent of the decline in BMC reported by Harris, et al., in the DSS induced mouse model of IBD (57%) [Harris, et al., (2008) see Table 2, col 1, line 1].

Although less statistically significant, the differences between the PEG treated groups and their respective untreated controls are consistent with a pattern of HMW PEG treatment generally improving BMC. HMW PEG treatment of fertile mice (control+PEG) resulted in a BMC level 129% of the untreated fertile mice (control). This is similar to the level of improvement seen in the OVX mice treated HMW PEG (OVX+PEG) relative to their untreated counterparts (OVX) of 123%. Most significantly, the data show that on average, treatment with HMW PEG restored OVX BMC to 76% of the control value. Thus, it appears that treatment with HMW PEG can generally increase BMC, but can also increase BMC in post-menopausal osteoporosis. In addition, this improvement is consistent with an increase in new bone synthesis, since the absolute increase in BMC appears to be dependent on how much bone the subject animal starts with, rather than on slowing resorption of existing bone.

3. Trabecular Bone Mineral Density of HMW PEG Treated Fertile and OVX Mice

Trabecular bone mineral density (BMD) content is representative of the amount of bone mineral present in a given volume of trabecular bone. Women who have had both ovaries removed are known to have lower BMD, and this is also shown in the OVX mouse model of FIG. 3. Comparison of the OVX sample group with the control group shows a statistically significant (p=0.0012) average decrease of just over 62%. This is consistent with the extent of the decline in BMD reported by Harris, et al. in the DSS induced mouse model of IBS (59%) [Harris, et al., (2008) see Table 2, col 1, line 2].

The difference between the control group and the control group treated with HMW PEG is not statistically significant; however it is consistent with the idea that HMW PEG treatment improves BMD. Here, on average, treatment with HMW PEG resulted in bone mineral densities about 115% of the untreated controls. The improvement in OVX mice is not only statistically significant (p=0.0005), but is also higher, with HMW PEG treatment resulting in 131% improvement in BMD relative to the untreated OVX group. The HMW PEG treated OVX mice had, on average, BMDs of about 82% of the untreated fertile mice. Thus, treatment with HMW PEG significantly increases BMD in animals suffering post-menopausal osteoporosis.

4. Cortical Bone Mineral Content of HMW PEG Treated Fertile and OVX Mice.

Cortical bone mineral content (CBMC) is a measure of the amount of bone mineral present across a given region of cortical bone. Although FIG. 4 shows little statistical or apparent difference between the control group average and the OVX group average in terms of CBMC, treatment with HMW PEG of either group results in increases in CBMC. In the case of the control and the control+PEG groups, treatment with HMW PEG resulted in about 115% CBMC over the control. However, this value is just beyond the statistical threshold of reliability (p=0.0593). A similar and statistically more robust improvement in CBMC is seen when the HMW PEG treated OVX group is compared with the OVX mice. In this case HMW PEG treatment resulted in about 118% CBMC over the OVX group (p=0.0022). Thus, treatment with HMW PEG improves CBMC.

5. Cortical Bone Mineral Density of HMW PEG Treated Fertile and OVX Mice.

Cortical bone mineral density (CBMD) is a measure of the amount of bone mineral present across a given region of cortical bone.

As with CBMC, there is little difference in CBMD between the control group and the OVX group shown in FIG. 5. However, treatment of each group with HMW PEG results in an increase in CBMD. A statistically significant (p=0.0110) improvement to 104% of the control group is apparent in the control+PEG group. A less statistically significant (p=0.0831), but slightly larger improvement to 105% of the OVX+HMW PEG group relative to the OVX group is also apparent. These are small differences relative to the observed changes in trabecular bone, but cortical bone is known to be much less dynamic, but the trend is consistent with HMW PEG improving CBMD.

6. Bone Volume Fraction of HMW PEG Treated Fertile and OVX mice.

Perhaps the most reliable indicator of changes in bone status is the bone volume fraction (BV/TV), which is the amount of mineralized bone per unit volume of sample.

FIG. 6 shows the significant differences in BV/TV between the OVX and control groups, with the OVX average BV/TV decreased to only about 38% of the control average (p=0.0008). Treatment with HMW PEG improves BV/TV in both control and OVX mice. In the case of the control mice, HMW PEG increases BV/TV to about 130% of the untreated group (p=0.0984). In the case of OVX mice, HMW PEG increases BV/TV to 189% of the untreated group (p=0.0017). This is an enormous improvement and the overall increase in BV/TV in the HMW PEG treated OVX group represents about 71% of the control group average. Thus, treatment with HMW PEG increases BV/TV in animals suffering post-menopausal osteoporosis.

7. Trabecular Thickness of HMW PEG Treated Fertile and OVX mice.

Individual trabs within trabecular bone vary in size and length within relatively narrow boundaries. Generally, the thicker the individual trab, the stronger the bone. Therefore, increases in average trabecular thickness (Tb.Th.) represent an improvement in bone status.

FIG. 7 shows the differences in Tb.Th. between the OVX and control groups. Relative to the control group average the OVX group has an average Tb.Th. of about 80%. As with the other markers of bone health discussed here, treatment with HMW PEG improves Tb.Th. In the case of the control mice, treatment with HMW PEG resulted in an average Tb.Th. about 113% of the control group average. In the case of the OVX mice, treatment with HMW PEG resulted in an average Tb.Th. about 122% of the OVX group average. Indeed, treatment of OVX mice with HMW PEG completely restores Tb.Th. to that seen in the control mice (relative ratio of 1.00). Thus, treatment with HMW PEG can increase Tb.Th. in animals suffering post-menopausal osteoporosis.

8. Trabecular Number of HMW PEG Treated Fertile and OVX Mice.

Another measure of trabecular bone health is trabecular number Tb.N., which reflects the number of trabs within a given area. The greater the number of individual trabs, the stronger the bone. Therefore, increases in Tb.N represent an improvement in bone status.

FIG. 8 shows the differences in Tb.N. between the OVX and control groups. Relative to the control group average the OVX group has an average Tb.N. of about 44%. Treatment with HMW PEG improved the Tb.N. of the control mice to 117% of the Tb.N. of untreated control mice. Treatment with HMW PEG of OVX mice increased the Tb.N. to 161% of the untreated OVX group. The Tb.N. of HMW PEG treated OVX mice represents 71% of the Tb.N. of the untreated control mice. Thus, treatment with HMW PEG can increase Tb.N. in animals suffering post menopausal osteoporosis.

9. Trabecular Spacing of HMW PEG Treated Fertile and OVX Mice.

Trabecular spacing (Tb.Sp.) is a measure of the void spaces within trabecular bone. Generally, the greater the Tb.Sp. the weaker the bone. Therefore, unlike the other measures of trabecular bone status discussed here, decreases in Tb.Sp. represent an improvement in bone status.

FIG. 9 shows the differences in Tb.Sp. between the OVX and control groups. The Tb.Sp. of OVX mice is more than twice (242%) that of the untreated control mice. Treatment with HMW PEG reduces Tb.Sp. in both the control and OVX groups. The control group treated with HMW PEG has a Tb.Sp. 71% of the untreated group, however these data are statistically unreliable (p=0.2356). The difference between the HMW PEG treated and untreated OVX groups is more pronounced, as well as statistically significant (p=0.0039). In this case, HMW PEG treated OVX mice have a Tb.Sp. about 139% of the untreated control mice, which represents a significant improvement over the untreated OVX mice. Thus, treatment with HMW PEG can decrease Tb.Sp. in animals suffering post menopausal osteoporosis.

10. Cortical Marrow Area of HMW PEG Treated Fertile and OVX Mice.

Cortical marrow area (CMA) is a measure of the area within cortical bone containing the marrow. As with Tb.Sp., the greater the CMA, the weaker the bone. Therefore, decreases in CMA represent an improvement in bone status.

FIG. 10 shows the differences in CMA between the OVX and control groups. There is little statistical difference between either the untreated control group and untreated OVX mice, OVX have a CMA about 107% that of the control group (p=0.5881). Treating the control group with HMW PEG actually appears to increase the CMA, with the treated control group having a CMA of 114% relative to the untreated control (p=0.2846). However, neither of these ratios is particularly meaningful given the high variance within the untreated control group, which results in poor group statistics on which to base a comparison. On the other hand, treatment of OVX mice with HMW PEG does result in a statistically meaningful (p=0.0419) decrease in CMA. In this case, treatment with HMW PEG results in OVX mice with a CMA 88% of the untreated OVX group. Thus, treatment with HMW PEG can improve CMA in animals suffering post menopausal osteoporosis.

11. Cortical Area of HMW PEG Treated Fertile and OVX Mice.

Cortical area (CA) is a measure of the bone area within a cross-section of cortical bone. Generally, the greater the CA, the stronger the bone. Therefore, increases in CA represent an improvement in bone status.

FIG. 11 shows the difference between OVX and untreated control is small, ratio of 98%, and not statistically significant (p=0.8095). The difference between control mice treated with HMW PEG and the untreated group is 111%, but also has only poor statistical significance (p=0.1529). As with the measurements of CA, this is primarily due to large deviations within the untreated control group. Better statistical confidence (p=0.0029) occurs in the comparison of OVX mice treated with HMW PEG compared with the untreated OVX group, which indicates that the HMW PEG treatment improves CA relative to the untreated mice to 112%, similar to the improvement seen between treated and untreated control mice. Thus, treatment with HMW PEG can increase CA in animals suffering post menopausal osteoporosis.

Taken together, these data demonstrate that treatment with HMW PEG improves many different parameters of both cortical and trabecular bone status in subjects suffering post menopausal bone loss. However, these measurement do not differentiate between changes in bone resorption and new bone synthesis.

Example 2

Effects of HMW PEG on Serum Osteocalcin in DSS and OVX+DSS Treated Mice

To determine whether the beneficial effect of HMW PEG treatment was due to inhibition of bone resorption or to induction of osteogenesis, the levels of serum osteocalcin were determined in treated and untreated mice with osteoporosis arising from different underlying conditions.

Sixteen female BALB/c mice were obtained from Jackson Laboratories (The Jackson Laboratory, Bar Harbor, Me.).). The mice were divided into two equal cohorts and the mice of one cohort overiectomized at ten weeks of age. Each cohort was further subdivided into two groups of four overectimized (OVX) mice and two groups of four fertile mice. One group of OVX and one group of fertile mice received HMW PEG through gavage (3× per week with 2 g/kg body weight HMW PEG). These animals also received 1% HMW PEG in D5W, provided ad libitum to maintain an effective amount of HMW PEG between gavage treatments. The other two groups were gavaged with equivalent volumes of water on the same schedule and provided with D5W. All four groups were given 1% DSS via their drinking water begin 15 days before the end of the experiment. This resulted in four groups, a control group of fertile mice unexposed to PEG (control+DSS), a group of fertile mice exposed to PEG (control+DSS+PEG), a group of OVX mice unexposed to PEG (OVX+DSS), and a group of OVX mice exposed to PEG (OVX+DSS+PEG). Throughout, the experiment animals were freely given standard chow and water and were maintained on a 12 hour light/dark cycle. All animal procedures were approved by the Michigan State University Institutional Animal Care and Use Committee.

Animals were euthanized at 14 weeks of age. Blood was sterilely collected at the time of harvest by cardiac puncture, allowed to clot at room temperature for 5 minutes and then centrifuged at 4,000 rpm for 10 minutes. Serum was removed, frozen in liquid nitrogen and stored at −80° C. Serum osteocalcin levels were measured using a Mouse OC assay kits (BT-470, Biomedical Technologies Inc., Stoughton, Mass.) according to the manufacturer's protocol.

FIG. 12 shows that the combined OVX+DSS group had substantially lower levels of serum osteocalcin than any other group of DSS treated mice, suggesting that the decrease in anabolic bone synthesis due to overiectomy was additive to any decrease caused by DSS alone. Treatment with HMW PEG restored serum osteocalcin to the same level as the control+DSS mice treated with HMW PEG. The serum osteocalcin levels of the control+DSS group are less than the PEG treated groups, but more than the OVX+DSS group. The fact that serum osteocalcin increases in response to HMW PEG treatment suggests that subjects treated with HMW PEG have a higher capacity for anabolic bone synthesis.

Example 3

Effects of HMW PEG on Serum Osteocalcin in Control, DSS and OVX+DSS Treated Mice To examine whether the beneficial effect of HMW PEG treatment on serum osteocalcin extended to healthy mice, and to provide a measure of the extent of the HMW PEG increase in serum osteocalcin in DSS and OVX+DSS treated mice, data from subjects from Example 1 and Example 2 were plotted relative to one another.

FIG. 13 compares serum osteocalcin levels of healthy control and control+PEG groups from Example 1 with the control+DSS and control+DSS+PEG groups from Example 2. Clearly the control group treated with HMW PEG has an increased average level of serum osteocalcin, although not within the desired statistical confidence level due to variance within the group. Likewise, the control+DSS+PEG group appears to have been restored to the same average level of serum osteocalcin as the healthy control group, but again without the desired level of statistical confidence. Although not statistically quantifiable, the benefit of HMW PEG treatment on serum osteocalcin is clearly apparent in these data. Significantly, treatment with HMW PEG increases serum osteocalcin even in mice with no underlying pathology.

FIG. 14 compares control and control+PEG groups from Example 1 with the OVX+DSS and OVX+DSS+PEG groups from Example 2. Here, as in the previous comparisons, treatment with PEG restores serum osteocalcin levels in the OVX+DSS group to the same level as the healthy control group average.

In light of reports that DSS induced IBS bone loss is due in large part to a decrease in the osteoblast osteogenic activity [Harris, et al., (2009); Hamdani, et al., (2008)], these data suggest that bone loss due to post menopausal factors is also due to reductions in osteoblastic osteogensis. The rebound in serum osteocalcin in subjects suffering from IBD induced osteoporosis (shown in FIG. 13) and even in subjects suffering from both IBD induced and post menopausal osteoporosis (shown in FIG. 14), upon treatment with HMW PEG indicates an increase in anabolic bone formation by osteoblasts.

Example 4

Effects of HMW PEG on the Feed Conversion Rate of Healthy and Infected Chickens.

The effect of HMW PEG treatment growth performance of broiler chickens raised under typical production conditions was tested. Four hundred and eighty chickens were randomly placed into 4 experimental groups, with 15 birds to each pen. All birds were raised from day of hatch under standard conditions of feed, water, light, air and temperature for 20 days. Birds in the negative control group received no special treatment. Birds in the 0.33% MDY(1-21) group were given HMW PEG MDY-1001 ad libitum as a 0.33% feed additive. Birds in the SE control group were infected with *Salmonella Enteritidis*, to provoke gastrointestinal disorder, but received no other special treatment. Birds in the 0.33% MDY(1-21)+SE group were infected with *S. Enteriditis* and were given HMW PEG (MDY-1001) ad libitum as a 0.33% feed additive. Feed consumption and body weight gain of each group was assessed at twenty days.

FIG. 15 indicates that although there is little statistical difference between the amounts of feed consumed by any of the groups, there is a significant improvement in the body weight of the chickens infected with *S. Enteritidis* treated with HMW PEG relative to those not treated. Thus, treatment with HMW PEG improves the feed conversion rate of animals experiencing a gastrointestinal disorder.

Example 5

Effects of HMW PEG on Recovery of Bacteria from Infected Chickens.

The effect of HMW PEG treatment on the ability of *Salmonella Enteriditis* to persist in infected chickens was examined Chickens were placed into 4 groups and raised under gastrointestinal inflammation of growth performance of chickens raised under the basic conditions described n Example 4. However, in this experiment all birds were infected with *S. Entiriditis* at the outset and the amount of bacteria recovered from the birds was measured after the treatment period. Birds in the control group received no special treatment. Birds in the 0.1%-T group were given HMW PEG ad libitum as a 0.1% feed additive. Birds in the 0.1%-P group were given a prophylactic ad libitum as a 0.1% feed additive. The number of colony forming units recovered from the cecum of each chicken was determined at the end of the treatment period.

FIG. 16 indicates that treatment with HMW PEG significantly reduced the bacterial load of infected chickens relative to uninfected chickens. Indeed, HMG-PEG treatment appears to have been more effective than the commercial prophylactic in reducing the bacterial burden. Thus, treatment with HMW PEG reduces the bacterial burden of animals exposed to infectious bacteria.

Example 6

Effects of HMW PEG on Cumulative Growth Performance of Weaned Piglets Exposed to Non-Specific Fecal Challenge.

The effect of HMW PEG treatment on growth performance of weaned piglets was tested by exposure to a non-specific fecal challenge on days 2-4 and 7 (post-weaning), by painting a slurry of fecal matter collected from a production-type nursery (1,100 pigs) to the inside of the feed pan in each pen. One hundred and sixty piglets were weighed on weaning, placed two to a pen with 20 replicate pens in each experimental group, fed their experimental diets for twenty days and then re-weighed. The positive control group was not subjected to the non-specific fecal challenge, whereas the negative control group and the two treatment groups were subjected to the fecal challenge. Treatment groups included one group receiving 35 g/ton Denagard® (12.5% tiamulin hydrogen fumarate antibiotic) and one group receiving 2% HMW PEG mixed directly into the feed. The frequency of scouring (diarrhea) in each group was also assessed by determining the scour score. Scour score is the number of scouring events divided by the total number of pens in each experimental group multiplied by one hundred.

TABLE I

Cumulative growth performance of weaned piglets exposed to non-specific fecal challenge.

|  | Positive Control | Negative Control | Negative Control + . . . | |
|---|---|---|---|---|
|  |  |  | 35 g/ton Denagard ® | 2.0% HMG-PEG |
| | | Weight (lbs) | | |
| day 0 | 14.7 | 14.3 | 14.9 | 14.8 |
| day 20 | 24 | 21.6 | 22.2 | 23.1 |
| | | Feed conv. (lbs/lbs) | | |
| | 1.13 | 1.31 | 1.40 | 1.44 |
| | | Scour score | | |
| | 1.05 | 1.19 | 1.13 | 1.06 |

The results, shown in Table 1, indicate that HMW PEG was slightly better than Denogard® in protecting the piglets from non-specific fecal challenge in terms of the absolute amount of weight gained by the piglets, the feed conversion rate (lbs feed/lbs piglet) and the scour score. The control piglets gained about 4.7 lbs/day, while the negative control piglets only increased their weight about 3.7 lbs/day. The piglets subjected to challenge and treated with Denagard® also only increased their weight about 3.7 lbs/day, whereas the piglets treated with HMW PEG increased by almost 4.3 lbs/day. More importantly, treatment with HMG-PEG reduced the incidence of scouring to the positive control level, indicating that HMG-PEG provides protection against the diarrhea associated with the stress of confinement and fecal contamination commonly present in high density swine operations.

The invention claimed is:

1. A method for treating osteopenia or osteoporosis comprising orally administering to an animal in need thereof a therapeutically effective dose of a composition consisting essentially of a high molecular weight polyethylene glycol (HMW-PEG) having an average molecular weight of between 15,000 daltons and 20,000 daltons, wherein the HMW-PEG comprises at least two hydrocarbon chains attached to a hydrophobic core, wherein each hydrocarbon chain has an average molecular weight of at least 40 percent of the HMW-PEG compound, and wherein the hydrophobic core comprises a ring structure.

2. The method of claim 1, wherein the animal is selected from the group consisting of dog, cat, horse, sheep, goat, cow, pig, chicken, turkey and human.

3. The method of claim 1, wherein the effective dose is sufficient to increase osteogenesis.

4. The method of claim 1, wherein the effective dose is sufficient to reduce bone resorption.

5. The method of claim 1, wherein the effective dose is sufficient to increase osteogenesis and reduce bone resorption.

* * * * *